United States Patent [19]

Keyes

[11] Patent Number: 4,714,676

[45] Date of Patent: * Dec. 22, 1987

[54] PROTEIN MODIFICATION TO PROVIDE ENZYME ACTIVITY

[75] Inventor: Melvin H. Keyes, Sylvania, Ohio

[73] Assignee: Owens-Illinois Glass Container Inc., Toledo, Ohio

[*] Notice: The portion of the term of this patent subsequent to Sep. 2, 2003 has been disclaimed.

[21] Appl. No.: 476,955

[22] Filed: Mar. 21, 1983

Related U.S. Application Data

[63] Continuation of Ser. No. 419,116, Sep. 16, 1982, abandoned.

[51] Int. Cl.$^4$ .................. C12N 11/14; C12N 11/02; C12N 9/00; C12N 9/14
[52] U.S. Cl. ......................... 435/176; 435/177; 435/183; 435/195; 530/402; 530/811
[58] Field of Search ............... 435/183, 184, 188, 199, 435/200, 201, 203, 176, 177, 195; 260/112, 121; 530/350, 362, 402, 811

[56] References Cited

U.S. PATENT DOCUMENTS 4,266,030 5/1981 Tschang et al. .................. 435/188
4,609,625 9/1986 Keyes et al. .................. 435/188 X

OTHER PUBLICATIONS

Yamauchi, et al., Reversible conversion of Lysine Monoxygenase to an Oxidase, *J. of Biol. Chem.*, vol. 248, 1973, pp. 3750 to 3752.

Mahler et al., *Biological Chemistry*, 1956, Harper and Row, N.Y. pp. 287-295.

Beaven et al., *International Journal of Peptide Research*, vol. 5, pp. 215-218, 1973.

Battelle Report, Verification of Semisynthetic Activity, Owens-Illinois, Jul. 14, 1981.

*Primary Examiner*—David M. Naff
*Attorney, Agent, or Firm*—H. G. Bruss

[57] ABSTRACT

A naturally occuring protein is chemically modified to provide the protein with activity of a selected enzyme. The protein does not contain activity of the selected enzyme before modification. Modification is preferably carried out by partially denaturing the protein in the presence of an inhibitor for the selected enzyme to form a partially denatured protein-enzyme inhibitor complex, adsorbing the complex to a solid support and crosslinking the adsorbed complex to form an immobilized modified protein having activity of the selected enzyme. Alternatively, the protein may be adsorbed onto the support, partially denatured and crosslinked in the presence of the inhibitor or the protein may be partially denatured, adsorbed on the support and crosslinked in the presence the inhibitor. In another embodiment, the protein has at least three disulphide groups. This protein is contacted with a disulphide bridge reducing agent in the presence of the inhibitor to produce a partially denatured protein-inhibitor complex, the complex is adsorbed onto a support and the adsorbed complex is contacted with a sulfhydryl oxidizing agent to form disulphide bonds in the protein to produce an immobilized modified protein having enzyme activity.

49 Claims, No Drawings

PROTEIN MODIFICATION TO PROVIDE ENZYME ACTIVITY

This is a continuation of application Ser. No. 419,116 filed Sept. 16, 1982, now abandoned.

BACKGROUND OF THE INVENTION

1. Field Of The Invention

Proteins are biologically synthesized macromolecules having various roles in living systems. Enzymes are particular varieties of biologically-active proteins which catalyze specific reactions. Presently, enzyme technology is used in many areas in industry and research, such as, for example, medical research, food processing and preservation, the production of fermented beverages, the production of pharmaceuticals and the analytical determination of the concentration of various metabolites and food components by analytical enzyme techniques Enzymes are highly specific in their biological activity and generally catalyze a particular reaction at a very high rate compared to the corresponding reaction occurring at room temperature without biological catalysis. One enzyme may show catalytic activity with respect to a number of substrates upon which it can act. Accordingly, a given enzyme may catalyze the synthesis or degradation of more than one substrate. Some proteins which are not considered classical enzymes, such as bovine serum albumin, show very limited catalytic activity with respect to one or more substrates.

Many enzymes are found in nature in very small quantities. Accordingly, their isolation, purification and use is limited to a small scale operation in view of the expense and time needed to isolate them in a useful form.

Some enzymes occur in nature in relatively large quantities and are relatively easy to isolate, purify and use. Unfortunately, due to the precise catalytic behavior of the enzymes, the enzymes available in large quantities can only catalyze certain select reactions.

Much effort has been directed in the recent past toward the synthesis of synthetic biological catalysts which exhibit enzymatic behavior similar to the enzymatic behavior exhibited by native enzymes which are either scarce or expensive to isolate. Further, some attempts have been made to modify native enzymes to change their enzymatic specificity so that they may function to catalyze a reaction which they previously could not catalyze.

2. Description Of The References

One technique known to achieve enzyme behavior to catalyze a specific desired reaction is the synthesis of so-called enzyme model molecules. For example, low molecular weight compounds may be covalently bonded to functional groups which exhibit the activity of the active site of an enzyme. Examples of such preparations are described in the publications: Breslow, R., *Advances in Chemistry Series*, R. F. Gould, Ed., American Chemical Society, Washington, D. C. 21–43 (1971) and Tang, C. C.; Davalian, D.; Haung, P. and Breslow, R., *J. Amer. Chem. Soc.*, 100, 3918 (1978) and Breslow, R., Doherty, J., Guillot, G. and Lipsey, C., *J. Amer. Chem. Soc.*, 100, 3227 (1978).

Another technique involves the use of a synthetic polymer matrix which is modified along its backbone to provide functional groups which exhibit the function of the active site of a given enzyme. Examples of such techniques can be found in the following articles: Wulff, G. and Schulza, I., *Israel J. Chem.*, 17, 291 (1978) and Suh, J. and Klotz, I. M., *Bioorganic*, 6, 165 (1977).

Another technique involves the attachment of a new chemical moiety to a native enzyme near the active site of the enzyme to attempt to cause such enzyme to react with a different catalytic activity. One example of this is the conversion of papain, a proteolytic enzyme to an oxidase type enzyme by the covalent attachment of a flavin near the active site of the native papain enzyme, as illustrated in the articles Levine, H. L. and Kaiser, E. T., *J. Amer. Chem. Soc.*, 100, 7670 (1978), Kaiser, E. T., et al, *Adv. In Chemistry Series*, No. 191, Biomimetic Chemistry, 1980; and Otsuki, T.; Nakagawa, Y. and Kaiser, E. T., *J.C.S. Chem. Comm.*, 11,457 (1978). Other examples of such enzymatic modification may be found in the article Wilson, M. E. and Whitesides, G. M., *J. Amer. Chem. Soc.*, 100, 306 (1978).

Still another attempt to change enzyme specificity is the immobilization of a native enzyme into a gel matrix. For example, trypsin enzyme has been immobilized in polyacrylamide gel. The polyacrylamide gel allows amino acid esters to diffuse through the gel matrix to react with the enzyme but will not allow larger proteins to diffuse through. Thus, the enzyme specificity is changed by eliminating access of one of the substrate molecules to the enzyme.

The immobilization of native enzymes is well established in the art. Also, examples of enzyme specificity changes by immobilization are known in the art. Both immobilization and enzyme specificity changes are described in the *Kirk-Othmer Encyclopedia of Chemical Technology*, 3 Ed., 9, 148 (1980) published by Wiley and Son, Inc.

Two other methods relating to enzyme immobilization are disclosed in U.S. Pat. Nos. 3,802,997 and 3,930,950. In U.S. Pat. No. 3,802,997, a method of stabilizing enzymes by bonding the enzymes to inorganic carriers, in the presence of their substrates, whereby the enzyme is immobilized, is disclosed. In U.S. Pat. No. 3,930,950, a method of enzyme immobilization is disclosed wherein an active support member is provided which is capable of reacting with an enzyme to become chemically bonded thereto. Subsequently, the active support is contacted with an enzyme-substrate complex which has been formed by mixing together an enzyme and a specific substrate, while minimizing the transformation of substrate to product. Thus, the enzyme component of the complex becomes chemically bonded to the support member.

Also, it has been known that a native lysine mono-oxygenase can be reacted to block the sulfhydryl groups on the enzyme. When the specific enzyme lysine mono-oxygenase is so treated, it shows new catalytic activity toward amino acids and catalyses oxidative deamination instead of its natural oxygenative decarboxylation. However, the reporters cannot account for the modified behavior. See the article by Yamauchi, T.; Yamamoto, S. and Hayaishi, O., in *The Journal of Biological Chemistry*, 248, 10, 3750–3752 (1973). Also, it has been reported that by reacting a native enzyme, for example trypsin, with its natural inhibitor, and subsequently cross-linking the enzyme, its activity with respect to its natural substrates can be modified. See the article by Beaven, G. H. and Gratzer, W. B. in *Int. J. Peptide Res.*, 5, 215–18 (1973).

Also, synthetic proteins have been synthesized by the anchoring of an amino acid residue on a solid support and subsequently adding amino acid residues one after another.

Further, semisynthetic proteins have been synthesized by a method wherein a native protein is subjected to limited hydrolysis to produce protein fragments. The fragments of the native protein are then subjected to a process whereby one or more amino acid residues are added or removed from the fragments to form modified fragments. The resultant modified fragments are then reattached to form the semisynthetic protein with an altered amino acid residue composition. Examples of the synthetic and semisynthetic protein technologies cited immediately above are found in the book *Semisynthetic Proteins* by R. E. Offord, published by John Wiley and Sons Ltd., copyrighted in 1980.

While these techniques are suitable for many applications, a need exists for a simple, efficient, economical and systematic method for chemically modifying an inexpensive and commercially available native protein to produce an enzyme-like modified protein. The protein can show a catalytic enzymatic activity with respect to a desired chemical reaction which was not previously a commercially-useful reaction catalyzed by the native enzyme and which new reaction can be predetermined in a systematic fashion. The methods disclosed in the above-disclosed references simply subject an enzyme to a set of conditions and attempt to eludicate its behavior. They fail to provide a systematic method to modify protein characteristics.

SUMMARY OF THE INVENTION

The present invention achieves an enzyme-like modified protein by converting a naturally occurring so-called native protein to an enzyme-like modified protein exhibiting different characteristics than the native protein starting material.

In one embodiment of the invention, a native protein is partially denatured in the presence of an inhibitor for the predetermined model enzyme, whose activity is to be modeled. Next, the partially denatured native protein, in the presence of the inhibitor of the model enzyme, is deposited on a solid support and cross-linked to define a new enzyme-like modified protein conformation which is defined by the inhibitor of the model enzyme and is preserved in an immobilized fashion on a solid carrier or support.

Subsequently, the inhibitor of the model enzyme and any excess cross-linking agent are removed from the newly formed, immobilized enzyme-like modified protein to yield a functional, stable, easy to process and isolate analogue to the model enzyme. The modified protein thusly produced exhibits the activity characteristics of the model enzyme.

DETAILED DESCRIPTION OF THE INVENTION

In attaining the advantages of the present invention, it has now been discovered that a protein can be modified from its native conformation to a modified conformation by practicing the process of the present invention. The new conformational state defines an enzyme like modified protein.

As used herein, the word "enzyme" is defined as a protein which has well-known catalytic activity toward specific substrates. The term "protein" as used herein is defined as generally accepted in the art, to wit, a polypeptide formed of amino acids to yield a biological molecule.

The process of the present invention comprises chemically modifying a native protein from one conformation, its natural or native state, to a second conformation, a new modified state. The process produces a new, enzyme-like modified protein which is produced and immobilized virtually simultaneously to yield a stable new enzyme-like modified protein which models one or more of the enzymatic activity characteristics of the selected model enzyme. I have discovered that a native protein can be converted to a modified protein and virtually simultaneously immobilized without any substantial adverse effects upon the conversion process or the immobilization process. No adverse steric or other structural problems militate against the preparation of a new enzyme-like modified protein when following my new process In the preferred embodiment of the invention, a native protein is selected which is to be chemically modified to produce the new enzyme like modified protein analogue of a desired model enzyme. The process of the present invention converts the soluble native protein, which does not possess the desired catalytic activity, namely the enzymatic catalysis behavior of the model enzyme, into a stable, immobilized enzyme-like modified protein which mimics or copies the biological catalytic activity characteristics of the model enzyme.

A preferred way of carrying out the novel process of the invention for chemically modifying a native protein to produce an immobilized predetermined enzyme-like modified protein comprises the steps of: partially denaturing the native protein in the presence of an inhibitor for the predetermined model enzyme; contacting the inhibitor bound partially denatured native protein with a solid immobilization support for a time sufficient and a temperature sufficient to produce an adsorption-immobilized native protein-inhibitor complex and subsequently cross-linking the support adsorbed, partially denatured protein-inhibitor complex to form the new, immobilized enzyme-like modified protein. Any excess cross-linking agent and the inhibitor are removed from the newly created immobilized modified protein to isolate the new catalytically active enzyme-like modified product protein.

While in the preferred embodiment, a non-enzymatic native protein is converted into an enzymatically reactive, immobilized enzyme like modified protein, the conversion of any native protein to an enzyme-like modified protein analogue of a model enzyme is contemplated herein.

As used herein, the phrase "partial denaturation" means a change in the conformation of a protein so as to perturb the natural shape or conformation of the protein without causing the irreversable, gross denaturation of the protein. As used herein, the word "conformation" is defined as generally accepted in the art, to wit, that combination of secondary and tertiary amino acid structure which produces a characteristic protein shape.

The partial denaturation of proteins is well known in the art and discussed in detail in the following references: The book *Biochemistry* by A. L. Lehninger, Worth Publishers, Inc., New York, N.Y., 1970, pg. 58; the article by P. L. Privalov entitled "Stability of Proteins" in *Advances in Protein Chemistry*, Vol. 33, pg. 167–192; the article by C. Sanford entitled "Protein Denaturation, Part C" in *Advances in Protein Chemistry*, Vol. 24, pg. 2–97; the article by F. R. N. Gurd, et al. entitled "Motions in Proteins" in *Advances in Protein Chemistry*, Vol 33, pg. 74–166; the article by O. Jardetzky in *BBA*, Vol. 621, pg. 227-232; the article by R. Huber in *TIBS*, Dec. 1979, pg. 271, and the article by D. S. Markovich, et al. in *Molekulyarnaya Biologiya*, Vol. 8, No. 6, pg. 857-863.

Also, as used herein, the phrase "denaturing agent" refers to process conditions or reagents which cause the partial denaturation of a protein. For example, the partial denaturation of a protein may be achieved by soaking the protein in an aqueous solution in an elevated temperature, for example, in the range of 25° C. to 60° C. For most protein, 25-60° C. will so perturb the conformational structure of the protein as to result in the partial denaturation of the protein. However, it is well known in the art, some proteins from thermophilic bacterial sources are stable to near the boiling point of water and would require higher elevated temperatures than those generally disclosed above.

The partial denaturation of a protein can be accomplished by soaking the protein in an aqueous solution containing an inorganic salt, in inorganic or organic acid or a water-miscible organic solvent.

Suitable inorganic salts which served to destabilize the protein structure for partial denaturation include: $NaF$, $(NH_4)_2SO_4$, $(CH_3)_4NCl$, $(CH_3)_4NBr$, $KCH_3COO$, $NH_4Cl$, $KCl$, $NaCl$, $CsCl$, $LiCl$, $KBr$, $NaBr$, $KNO_3$, $MgCl_2$, $NaNO_3$, $CaCl_2$, $KSCN$, $NaSCN$, $BaCl_2$, $NaI$ and $LiI$.

Suitable inorganic acids include: hydrochloric, nitric, sulfuric, phosphoric and similar proton donating strong inorganic acids.

Suitable organic acids include: acetic, formic, propionic and acitric acid.

Suitable water-miscible solvents for protein denaturation include: t-butanol, acetonitrile, dioxane, acetone, methanol, ethanol and dimethylsulfoxide.

As used herein, the tere "inhibitor" means any compound with sufficient structural similarity to the natural substrate of a model enzyme to serve as a template for the catalytic site of the enzyme-like modified protein. In the preferred embodiment of the preparation of an enzyme-like modified protein, the inhibitor is any of the known classical inhibitors for a given model enzyme. However, as used herein "inhibitor" can include any molecule with sufficient structural similarity to the classical inhibitor to preserve an inhibitor like site on the modified protein. The natural substrate of the model enzyme can act as the inhibitor or template for the modified protein in many cases. Inhibitors are generally not degraded by the enzyme, as are substrates, and serve to more readily preserve a catalytic site than the natural substrate. One example of the structural similarity of an enzyme inhibitor and the natural substrate of an enzyme is the case of glucose oxidase. Glucose is the natural substrate of glucose oxidase while D-glucal is the inhibitor for glucose oxidase. Glucose and D-glucal are very structurally similar.

In the preferred embodiment of the present invention, the forming enzyme-like modified protein is immobilized on a solid support which is usually inorganic in composition. Particularly preferred are inorganic water insoluble supports such as refractory ceramic oxides. Suitable ceramic oxides include porous, particulate ceramic oxides which can be formed by compacting and sintering refractory ceramic oxide powders such as alumina powder, zirconia powder, magnesia powder, silica powder and thoria powder. Alumina powder is particularly preferred due to its chemical durability and low cost. The preparation and use of such ceramic alumina and other ceramic oxide supports such as disclosed in U.S. Pat. No. 4,001,085.

As used herein, the term "cross linking" means the formation of covalent bonds between reactive sites on a protein. Generally, protein cross-linking is accomplished by the use of multifunctional reagents such as glutaraldehyde. Other examples of suitable cross-linking reagents to effect the cross-linking of a protein are: 2-amino-4, 6-dichloro-s-triazine; diazonium salts; N-hydroxysuccinamide; p-benzoylazide and those reagents disclosed in the following referencee: Wold, F., *Methods Enzymol*, 11, edited by C. H. W. Hirs, C.H.W., Academic Press, 1967, 617; Fasold, H. et al., *Augen. Chem. Int. Ed. Engl.*, 10, 795, 197 and Keyes, M. H., in the Kirk-Othmer *Encyclopedia of Chemical Technology*, 9, 3rd Ed., 1980, J. Wiley & Sons, Inc., 148-172.

In an alternative embodiment of cross-linking of the partially denatured protein, the cross-linking of the protein after it has been partially denatured and subjected to inhibitor contact may be achieved by disulphide rearrangement when the native protein being converted to an enzyme-like modified protein analogue of a model enzyme is rich in disulphide bridges. Such disulphide rearrangement is accomplished by subjecting the native disulphide bridge rich protein, at about neutral pH, to various reagents to break the disulphide bridges to yield sulphydryl groups. A preferred reagent is beta-mercaptoethanol. The beta mercaptoethanol cleaves the disulphide bridges, thereby loosening the conformational structure of the protein and partially denaturing the protein by the formation of sulphydryl groups. After the protein has been subjected to contact with the inhibitor of the model enzyme, the sulphydryl groups may be reduced to the disulphide form to relink the protein into a new, stable enzyme-like modified protein. Such relinking of sulphydryl groups in disulphides may be easily accomplished by raising the sulphydryl containing protein to an elevated pH. A pH value of between 9 and 10 is usually quite acceptable. It should be noted, however, that molecular oxygen is usually a reactant in a sulphydryl reaction to form disulohide bridges so the high pH reaction should be carried out in the presence of molecular oxygen. Other oxidizing agents which are known to oxidize sulphydryl functions to the corresponding disulphide are equally operative.

In the preferred embodiment of the invention, a native or host protein showing little or no catalytic activity is converted chemically by the process of the present invention into an enzyme-like modified protein analogue of a model enzyme. Many enzymes are susceptible to modeling by the present process to produce their enzyme-like modified protein analogues from selected native protein starting materials. Examples of such model enzymes which are subject to enzyme-like modified protein analogue production are hydrolytic enzymes, redox enzymes and transferase enzymes. By way of example: The first group, hydrolytic enzymes include proteolytic enzymes which hydrolyze proteins, e.g., papain, ficin, pepsin, trypsin, chymotrypsin, bromelin, keratinase; carbohydrases which hydrolyze carbohydrates, e.g., cellulase, amylase, maltase, pectinase, chitanase; esterases which hydrolyze esters, e.g., lipase, cholinesterase, lecithinase, alkaline and acid phosphateases; nucleases which hydrolyze nucleic acid, e.g., ribonuclease, deoxyribonuclease; and amidases which hydrolyze amines, e g., arginase, asparaginase, glutinase, histidase, and urease. The second group are redox enzymes that catalyze oxidation or reduction reactions. These include glucose oxidase, xanthine oxidase, catalase, peroxidase, lipoxidase, and cytochrome reductase. In the third group are transferase enzymes that transfer groups from one molecule to another. Examples of these are glutamicpyruvic transaminase, glutamicoxalacetic transaminase, transmethylase, phosphopyruvic transphosphorylase.

In the usual practice of the present invention, one selects a first or model enzyme. One then selects a second native host protein to be modeled after the model enzyme to produce an enzyme-like modified protein. In many cases the native protein is itself enzymatically active since many common enzymes are available in large quantities at fairly low costs in homogeneous sample form. However, nonenzymatic proteins are equally useful when they can be purified for use with the present process. One example of such a nonenzymatic protein which may be used as a native protein for the starting material of the bovine serum albumin (BSA). BSA is available in relatively pure form at fairly low cost from numerous commercial sources.

By practicing the process of the present invention, one can custom-tailor the native protein to a different immobilized, stable enzyme-like modified protein form which shows the catalytic activity characteristics of the enzyme which has been modeled. The ability to custom-tailor a native protein into a predetermined catalytic activity provides greater advantages in a wide range of chemical and industrial situations. For example, if one wishes to use an enzyme which is in short supply, is very expensive or very difficult to isolate and/or purify, such an enzyme may serve as a model enzyme for the preparation of an enzyme-like modified protein analogue by the present process to mimic its activity.

The present invention advantageously converts a native protein in a virtually simultaneous conversion and immobilization sequence of steps into an immobilized, stable easily recoverable, modified protein form which mimics the desired characteristics of the model enzyme.

Thus, a native protein which is available in large quantities or at low cost can be reformed or modified by the process of the present invention to convert the available native protein into an enzyme-like modified protein form of a less available and/or more expensive enzyme.

In the preferred embodiment of the invention, a native protein is purified and dissolved in a near neutral aqueous solvent in the presence of a suitable buffer to maintain the solution near neutrality. Subsequently, the native protein is partially denatured by any of the expedients described hereinabove, for example, lowering the pH or subjecting it to partial denaturation agents, to produce a partially denatured, soluble form of the native protein. Subsequently, an inhibitor for the model enzyme is admixed with the partially denatured protein. Next, a support, for example, a particulate porous alumina material, is admixed with the partially denatured native protein in the presence of the inhibitor for the model enzyme. Sufficient time and sufficient temperature are provided for the partially denatured protein-inhibitor complex to form and absorb onto the surface of the porous particulate support. Subsequently, to preserve the new, enzyme-like modified protein, the partially denatured native protein-inhibitor complex must be stabilized.

The new protein is stabilized by cross-linking of the protein to produce the enzyme like modified protein. Often, cross-linking is done as disclosed above by glutaraldehyde cross-linking agent or sulphydryl rearrangement since both are relatively inexpensive to achieve. However, any of the above-described cross-linking agents can be utilized effectively in the conventional manner.

In an alternative embodiment of the simultaneous preparation and immobilization of an enzyme-like modified protein, a native, nonpartially denatured protein is adsorbed onto the surface, interior and/or exterior, of a porous particulate ceramic oxide support. The immobilized, native protein is subsequently subjected to partial denaturation by any of the above described reagents. The partially denatured, adsorption immobilized protein is subsequently admixed with the inhibitor of the model enzyme to form the partially denatured protein-inhibitor complex. After the partially denatured native protein-inhibitor complex is formed, already being immobilized on the support, cross-linking is conducted as disclosed above.

In yet another embodiment of the invention, it has been discovered that the native protein may be partially denatured, adsorbed onto a porous particulate support, and thereby immobilized, with subsequent contacting of the inhibitor to the partially denatured immobilized protein. Subsequently, the partially denatured native protein-inhibitor complex is cross-linked to produce a new enzyme-like modified protein.

In still another embodiment of the invention, it has been discovered that the stable, immobilized, enzyme-like modified protein of the present invention may be produced by admixing together a partially denatured native protein with the inhibitor of the model enzyme to form a soluble partially denatured native protein-inhibitor complex. Subsequently the complex is adsorbed onto the support. Thereafter, the complex is cross-linked to produce the new, enzyme-like modified protein according to the present invention.

It has been discovered according to the present invention that it is possible to prepare an enzyme-like modified protein in still another embodiment. It has been discovered that a native protein may be reacted with succinic anhydride, at low pH, for example about pH 4, to produce new negatively charged carboxylic acid sites on the protein. The carboxylic acid sites which are produced by succinic anhydride reaction are formed by the reaction of the anhydride function on the succinic anhydride with free amine groups on the protein. This reaction converts positive amino groups on the protein to negative carboxylic acid moieties. This conversion is advantageous since generally ceramic oxide supports, the preferred supports of the invention, at low pH are positively charged. By forming more negatively charged groups on the surface of the native protein, a greater the electrostatic interaction then exists between the support and the protein, which is to be immobilized, thereby assisting in the formation and maintenance of protein immobilization.

Also, it has been discovered that enzyme-like modified protein production can be enhanced by the use of various bridging groups to span between carboxylic acid residues on the protein to help cross-link protein (whether the carboxyl groups are native to the protein or are anhydride derived) to form the new, stable, enzyme-like modified protein structure. One such bridging group is diaminopropane-HCl in the presence of a carbodiimide. Suitable carbodiimides include ethyl-3-(3-dimethylaminopropyl)-carbodiimide. Diaminopropane supplies amine groups which react with the native or newly formed, succinic anhydride derived, carboxyl groups on the native protein to produce covalent bonds. Accordingly, the succinic anhydride created carboxyl groups on the protein serve not only to electrostatically anchor the protein to the support but a portion of such groups also provide reactive sites to cross-link the protein by reacting with the diaminopropane amino groups.

Also, it has been discovered that enzyme-like modified protein production is enhanced by the use of carbodiimides. Such carbodiimides react with protein amine and carboxylic acid functions to produce covalent bonds. Such peptide bond formation assists in the cross-linking of the newly formed, modified protein to stabilize their structure.

It has been discovered according to the present invention that it is not particularly critical to admix succinic anhydride and the diaminopropane in any particular order with the native protein. For example, the native protein may be reacted with succinic anhydride to produce carboxyl groups, immobilized, reacted with diaminopropane and subsequently reacted with a carbodiimide to produce an cross-linked enzyme-like modified protein. Alternatively, the native protein may be reacted with the succinic anhydride, subsequently with the diaminopropane, then immobilized and subsequently reacted with the carbodiimide Also, the native protein may be partially denatured, contacted with the inhibitor, subsequently immobilized and then in a one step process reacted with a succinic anhydride and carbodiimide combination reagent to produce the cross-linked new enzyme-like modified protein.

The process of the present invention produces a new, enzyme-like modified protein which exhibits a number of advantages and uses. By the discoveries of the present invention, an immobilized, enzyme-like modified protein can be produced which is stable, easily recoverable and recyclable and exhibits a new enzyme-like catalytic activity which was not present in the native protein. Such modified proteins showing enzyme-like catalytic behavior are useful to perform catalytic anabolic and catabolic reactions instead of a naturally ocurring enzyme In all embodiments of the present invention the inhibitor of the model enzyme is removed after synthesis of the enzyme-like modified protein. Typically repeated washings of the immobilized modified protein is sufficient to remove the inhibitor. Buffered aqueous solution can also be used to remove the inhibitor, such buffers are exemplified hereinafter.

For convenience of disclosure, all patent documents and publications mentioned herein above are incorporated by reference.

Other embodiments of the present invention will be apparent to those of ordinary skill in the art from a consideration of this specification or practice of invention disclosed herein. It is intended that the Examples in the specification be considered as exemplary only with the scope and spirit of the invention being indicated by the claims. The following Examples are exemplary of the various embodiments of the process of the present invention discussed hereinabove.

EXAMPLE 1

Ten g of Kimal TM (−80+100 mesh) porous particulate alumina immobilization support from Owens-Illinois, Inc. is washed three times with distilled water.

Porous, inert, rigid, dimensionally stable refractory fluid permeable support particle can be prepared by compacting such refractory oxide powders to form a "green compact" of the desired configuration. The green compacts are then fired for a time and at a temperature sufficient for sintering to yield porous, inert, rigid, dimensionally stable, fluid permeable refractory particulate support. The sintering should not be at a temperature or for a time which would cause collapsing or coalescence of the particles to form a non-porous body. A convenient indication of the degree of sintering is a comparison of the actual density of the fired compact as compared to the theoretical density of the oxide being fired. Of the many oxides which can be used for the present purposes, alumina is preferred for its chemical durability and ease of fabrication.

In forming the particulate support from the powdered refractory oxide, the powdered particle size is selected to yield a sintered compact having a porosity and pore size in the desired range. The techniques for compaction and sintering of the porous supports are well-known in the art and form no part of the present invention. Suffice it to say that compacting pressures in the range of 1,000 p.s.i. to 10,000 p.s.i. and sintering temperatures in the range of 1,300° to 1,700° C. are commercially expedient. Additional details on compacting and sintering of refractory oxides can be obtained from the book "Oxide Ceramics" by E. Ryshkewitch, published in 1960 by Academic Press, New York, N. Y.

Next, 0.5 g of bovine serum albumin (BSA) from Sigma Chemical Company (Sigma) Type A-6003, lot 110F - 9305 is dissolved in 50 ml of 1 mM (ionic strength) 2-amino-2 (hydroxymethyl)-1,3-propanediol (tris) buffer at pH 7.5. The 50 ml of solution is added to the washed alumina support with a resulting pH of 7 5. The absorbance at 280 nm is 6.62. Then, 0.5 ml of a 0.2 M solution of beta-mercaptoethanol (BME) is added to the solution above the Kimal TM alumina support and the resulting solution is shaken for 0.5 hours. After 0.5 hours, the pH is 7. Next 0.333 g of tryptamine inhibitor for esterase is added and the resulting pH is 7.2. The solution is then stirred for 0.5 hours and then the pH is raised to 8.7 with 0.01 M NaOH.

The solution is then shaken for an additional 1.5 hours. After 1 5 hours of shaking the support with the bound esterase-like modified protein is washed five times with 1 mM tris at pH 7.5 containing 1% tryptamine inhibitor and 30% sucrose and stored in the same solution until needed.

The esterase like modified protein prepared above is assayed as follows. Twenty-five ml of 1 mM L-tryptophan solution is prepared by dissolving 0.005 g in distilled water and adjusting to volume in a 25 ml volumetric flask. Then, 25 ml of 0.01 M L-tryptophan methyl ester (TME) substrate is prepared by dissolving 0.0637 g in distilled water and adjusting to volume in a 25 ml volumetric flask. One l of 1 mM tris buffer is prepared by adjusting one l of distilled water to pH 3 with 1 N HCl then readjusting to pH 7.5 with tris buffer. Three l of 0.03 M acetate eluant is prepared by dissolving 12 g of sodium acetate trihydrate and 0.2 ml of glacial acetic acid in 3 l of distilled water. The resulting element solution is at pH 6.1

The assay is performed on a high pressure liquid chromatograph. The column is packed with porous silica containing carboxyl side chains from Baker Chemical Company. The injected sample is delivered from a 0.02 ml sample loop.

The column retention times for 1 mM L-tryptophan; 0.01 M TME and 50/50 mixture of each is determined as standards.

Next a control solution for the assay is prepared by mixing 1 ml of 0.1 M TME into 9 ml of 1 mM tris buffer pH 7.0. The pH of the solution is 5.8.

The sample solution of 10 ml is prepared by adding 0.5 to 1 g (dry weight) of the immobilized enzyme like modified protein prepared above to 9 ml of 1 mM tris buffer pH 9.0 and 1 ml of 0.1 M TME. The pH of the solution is 5.8.

The pH of the sample and control solution must be the same for the chromatographic assay. Generally, the sample shows a higher pH than the control after being stored in refrigeration for a period of time. The higher pH can be lowered by decanting the solution from the solid support material and replacing it with new control solution. This is repeated until the pH of the sample and controls, are nearly the same. Since the new esterase enzyme-like modified protein is immobilized on the support, no adverse effect is seen by multiple solution changes.

Injection of control and sample are made onto the column. The concentration of L-tryptophan is plotted on the y-axis and time of elution on the x-axis of a graph.

Activity for the support immobilized esterase enzyme-like modified protein is calculated according to the following formula.

$$\text{Activity} = \frac{[(\text{change in } S \pm \Sigma \delta m) \times 10^{-5}][10^{+6}][10^{-2}]}{\frac{\text{dry weight of support in g}}{2.6}}$$

wherein:
Activity is in Units/ml of support;
change in S is the change in slope in molarity;
$\Sigma \delta m$ is the sum standard deviation of the slopes for the sample a and control;
$10^{+6}$ is micromoles;
$10^{-2}$ is the volume of sample in l; 2.6 is the density of the support in g/ml; and
U is micromoles/minute
The assay results are as follows:

| | Substrate | |
|---|---|---|
| | | TME (U/ml support) |
| Initial Activity | | 0.00 |
| Final Activity | Assay 1 | 3.9 ± 1.9 × 10⁻³ |
| | Assay 2 | 5.3 ± 0.61 × 10⁻³ |
| | Assay 3 | 8.8 ± 1.19 × 10⁻³ |
| | Assay 4 | 4.9 ± 1.14 × 10⁻³ |

The results show that the modified esterase enzyme-like protein prepared according to the invention exhibits activity toward esterase substrate TME where no activity is previously detected in the native BSA. This illustrates the conversion of one genus of nonenzymatic protein, an albumin, to another genus of protein, an enzymatically active esterase enzyme-like modified protein.

EXAMPLE 2

Sixty mg of ribonuclease, from Sigma, No.R 5503 Type 1AS, lot 20-F 81001, is dissolved in 100 ml of distilled water The resulting solution is at pH 4.7 and has an absorbance at 280 nm at 0.313. Next, 0.3 ml of 0.2 M beta mercaptoethanol disulphide bridge cleaving reagent is added, with the pH of the solution lowering to 4.4. Next, the pH of the solution is returned to 7.0 by the addition of 1.3 ml of 0.01 N NaOH and maintained thereat for 2 hours. After the two hours, 40 mg of indole inhibitor is added which requires 1.25 hours to dissolve. Also, 3 ul (microliters) of 0.01 N NaOH is added to maintain the pH at 7.0.

Subsequently, the pH of the solution is raised to 9.45 with the addition of 4.7 ml of 0.01 M NaOH. The solution is maintained at pH 9.45 for three hours which requires the addition of 0.9 ml of the 0.01 M NaOH over the 3 hour period. Next, 20 g of Kimal TM (−80+100 mesh)is added to one-half of the above solution. Next, 0.4 g of 0.01 N NaOH is added to bring the pH of the resulting support-protein mixture to 9.45. Next, 0.01 ml of 1 mM succinic acid reagent (used to relink sulfhydryl groups into disulphide bridges) and 0.025 g of ethyl-3 (3 dimethyl-aminopropyl)-carbodiimide (EDC) (cross-linking agent) is added to the solution. The pH of the solution after 15 minutes is 7.15. After the 15 minute period, 5 ml of 5 percent (W/W) EDC is added at a rate of 0.1 ml per min. The solution is allowed to react overnight (about 17 hours) on a cold (0°-5° C.) shaker. After the reaction time, the pH of the solution containing the newly synthesized, cross-linked, immobilized enzyme-like modified protein is 6.4. The pH of the solution is then returned to pH 7 by the addition of 0.4 ml of 0.01 N NaOH. The immobilized enzyme-like modified protein is washed 5 times with one mM tris buffer at pH 7 containing 0.04% indole inhibitor. The inhibitor solution is believed to stabilize the desired conformation of the newly synthesized enzyme-like modified protein during storage.

The assay for enzymatic activity of a new synthesized enzyme-like modified protein is performed on a high pressure liquid chromatograph. The analysis is identical to the analysis disclosed in Example 1, above, except that the eluant is 5 mM tris at pH 8.0 and the substrate is 0.0115 M tryptophan methyl ester (TME).

The assay results are as follows:

| | Substrate | |
|---|---|---|
| | | TME (U/ml support) |
| Initial Activity | | 0.00 |
| Final Activity | after 1 day | 0.51 |
| | after 2 days | 0.43 |

The above results demonstrate that the esterase-like modified protein prepared according to the present invention exhibits enzymatic activity with respect to esterase substrate TME. No such activity is previously detected in the native ribonuclease. This illustrates the conversion of one genus of enzyme, a nuclease, to another genus of protein, an esterase enzyme-like modified protein.

EXAMPLE 3

Sixty mg of ribonuclease, from Sigma, Type R-5000-IIA, lot 110-F02051, is dissolved in 50 ml of distilled water. The initial pH of the solution of ribonuclease is 4.6 with a 280 nm absorbance of 0.693. After a 15 minute waiting period, 0.1 ml of a 0.1 M BME solution is added with slow stirring at 25° C. The pH of the solution is immediately raised to 7.0 with the addition of 0.1 M NaOH. The resulting neutral solution is stirred for one hour at about 25° C. Next, 10 mg of indole inhibitor is added and the solution stirred for 1.5 hours. During the stirring period, the pH of the solution is slowly raised to 8.2 with the dropwise addition of 0.1 M NaOH. After the 1.5 hour stirring period, the pH of the solution is slowly raised to 9.45 over a one hour period and maintained thereafter for an additional 2 hours with the dropwise addition of 0.1 M NaOH.

Subsequently, 10 g of Kimal TM alumina support (−80+100 mesh) is added to the partially denatured inhibitor bound enzyme solution. The resulting mixture is placed on a cold shaker at 0°–5° C. When the temperature of the solution reaches 5° C., 0.1 ml of 8% glutaraldehyde solution is added. The mixture is allowed to react overnight (about 17 hours) at 0°–5° C. with slow shaking The assay for enzymatic activity of the newly synthesized esterase enzyme-like modified protein prepared according to the present invention is performed on a high pressure liquid chromatograph. The procedure used in this Example is identical to the procedure used in Example 1.

The assay results are as follows:

| | Substrate |
|---|---|
| | TME (U/ml support) |
| Initial Activity | 0.00 |
| Final Activity | 0.52 |

The results show that the esterase enzyme-like modified protein prepared according to the present invention exhibits enzymatic activity with respect to esterase substrate TME. No activity is previously detected in a native ribonuclease. This illustrates the conversion of one genus of enzyme, namely, a nuclease, to a second genus of protein, namely, an esterase enzyme-like modified protein.

EXAMPLE 4

Sixty mg of ribonuclease, from Sigma, lot no. 20F-81001, is dissolved in 100 ml of distilled water. The absorbance is 0.333 at 280 nm, with a pH of 4.6. Next, 0.3 ml of 0.2 M BME is added. The solution is allowed to stand for 5 minutes. After 5 minutes, the pH of the solution is 4.7. The solution is then adjusted to pH 7 by adding 2.8 ml of 0.01 N NaOH. The solution is maintained at pH 7 for 2 hours by the addition of 0.01 N NaOH. The addition is occasionally unnecessary due to the natural raise in pH from about 7 to about 7.2. However, if the pH does not spontaneously elevate, the addition of the NaOH is necessary. Next, 20 g of washed Kimal TM (−80+100 mesh) is added to the solution at pH 7.2. The pH of the solution slowly rose to 7.7 after the addition of the solid alumina support.

The ribonuclease enzyme in the presence of the alumina support, is bound to the inhibitor for the model enzyme as follows. About 0.04 g of indole inhibitor is added to the solution at pH 7.7. The solution is maintained at pH 7.7 for 15 minutes. Then, the solution is raised to pH 9.45 by the addition of 20 ml of 0.01 N of NaOH.

The support bound partially denatuaed enzyme, in the presence of indole inhibitor, is cross linked by maintaining the solution at 9.45 for 2 hours at room temperature. The 2 hour period at elevated pH allows the sulfhydryl groups to rearrange to form disulphide bridges to intramolecularly cross-link the newly synthesized esterase-like modified protein.

After the 2 hour period, the solution containing the immobilized esterase-like modified protein is decanted and the support, with the bound new enzyme-like protein thereupon is washed repeatedly with two l of a 1 mM solution of tris buffer at pH 7 containing 0.04% indole. The thusly produced solid support bound esterase-like modified protein can be stored under refrigeration in the tris buffer indole solution until used.

The activity of the support immobilized esterase-like modified protein prepared according to the present invention is determined by high pressure liquid chromatography. The procedure used to determine the activity of the newly synthesized enzyme like modified protein prepared according to the present invention used in this Example is the same procedure used in Example 1, above.

The assay results are as follows:

| | Substrate |
|---|---|
| | TME (U/ml support) |
| Initial Activity | 0.00 |
| Final Activity (days) | |
| 1 | $11.97 \pm 0.937 \times 10^{-3}$ |
| 3 | $5.78 \pm 1.64 \times 10^{-3}$ |
| 8 | $7.56 \pm 1.90 \times 10^{-3}$ |
| 10 | $7.22 \pm 1.80 \times 10^{-3}$ |
| 11 | $8.65 \pm 1.60 \times 10^{-3}$ |

The results illustrate that the esterase enzyme-like modified protein prepared according to the present invention exhibits enzymatic activity with respect to esterase substrate TME. No activity is previously detected in the native ribonuclease. This illustrates the conversion of one enzymatic genus, namely, a nuclease, to a second genus of protein, namely, an esterase-like modified protein.

EXAMPLE 5

Five hundred mg of bovine liver catalase enzyme, from Sigma type C-40, lot 109C-7370, is dissolved in 200 ml of distilled deionized water with slow stirring at 25° C. The pH of the resulting solution is 6.5. Next, to partially denature the catalase enzyme, 10 mg of succinic anhydride is dissolved in one ml of acetone. Three hundred ul of the succinic anhydride-acetone solution is added to the catalase solution every 10 minutes. After the commplete addition of all of the succinic anhydride-acetone solution, the pH of the resulting solution is 4.0 and the solution is slightly turbid.

Next, galactosidase inhibitor, namely, D-galactal is added to the above solution as follows. Two hundred fifty mg of the D-galactal, from Koch-Light Laboratories, Ltd. lot 56129, code 2836h, is added and the solution is stirred for 15 minutes at 25° C. Next, 25 g of Kimal TM solid alumina support (−70+80 mesh) from Owens-Illinois, Inc. Toledo, Ohio, coated with diethylaminoethyl-dextran (DEAE-dextran) is then added and the mixture is gently shaken for 30 minutes at 25° C.

The DEAE-dextran coated support is prepared as follows. Two hundred 9 of porous alumina (−40+50 mesh, Kimal TM brand from Owens-Illinois, Inc.) is washed repeatedly with distilled deionized water until clean of fines. Then 20 g of sodium sulfate is dissolved in 500 ml of distilled, deionized water and mixed with the 200 g of alumina support while stirring at 25° C. Then, 10 g of sodium hydroxide is dissolved in 250 ml of distilled deionized water and 32 g of DEAE-dextran (from Sigma type 0-4885, lot 87 C-0139) is slowly added. The alumina-sodium sulfate mixture and the DEAE-dextran solution are then mixed together and shaken gently for 2 hours at 25° C. Next, 10 g of sodium hydroxide is dissolved in 250 ml of distilled, deionized water and 40 ml of epichlorohydrin is added while stirring at 25° C. The epichlorohydrin solution is then mixed with the DEAE-dextran alumina support mixture and the entire mixture is shaken gently for 24 hours at 25° C. After the 24 hour shaking period, the preparation was extensively washed with distilled, deionized water until clear. The newly formed DEAE-dextran coated alumina support can be stored under refrigeration (at 0°-5° C.) in distilled, deionized water until ready for use.

After the addition of inhibitor and absorption of the partially denatured native catalase enzyme onto the alumina support, the catalase is cross-linked onto the support as follows.

Ten mg of diaminopropane-HCl is dissolved in 25 ml of distilled, deionized water. One ml of this solution is then added to the preparation containing the support and shaken for one hour. The pH of the preparation is raised from about 4.0 to about 7.0 with the dropwise addition of 0.1 M NaOH. The DEAE-dextran coated alumina support is green in color and the turbidity of the supernatant liquid disappears. Next, 500 mg of 1-ethyl-3-(3 dimethylaminopropyl) carbodiimide hydrochloride (EDC) is then added and allowed to react for 3 hours at 25° C., with gentle shaking. After the 3 hour reaction period, the supernatant liquid is clear. The support with the immobilized and cross-linked enzyme-like modified protein thereupon is then washed with 1 l of distilled, deionized water; then 1 l of 0.2 M (NH4)2SO4 and finally with 1 l of distilled, deionized water. The preparation is stored under 1% D-galactal inhibitor solution at 0°-5° C., pH 6, in order to stabilize the newly formed enzyme-like modified protein which is cross-linked and immobilized on the support, as discussed above.

The assay for the enzyme-like modified protein activity is performed as follows. A reaction solution for the assay is prepared by mixing 10 ml of 0.002 M sodium phosphate buffer at pH 7.5 with 15 ml of distilled, deionized water and 5 ml of 0.014 M o-nitrophenyl-B-D-galactoside substrate solution in a 50 ml beaker.

Three ml of the solution is then placed in a cuvette and the cuvette is placed in a spectrophotometer (Beckman Instruments Company, Model ACTA III) wherein a baseline is recorded for three minutes at 405 nm to establish a stable baseline. Next, approximately 1 g of the immobilized enzyme-like modified protein prepared according to the present inventions is washed with distilled, deionized water and added to the substrate solution. Every minute, 3 ml of substrate solution is withdrawn and the absorbance measured at 405 nm and the results recorded. The 3 ml of substrate solution is then returned to the reaction flask. This procedure is repeated 6 times. The resulting slope due to the increase of absorbance per minutes gives an activity for the enzyme-like modified protein prepared according to the present invention vs. the substrate o-nitrophenyl-beta-D-galactoside. The increase in absorbance over a 6 minute period is measured to be 0.015.

The control assay for DEAE-coated alumina support vs. orthonitrophenyl B-D-galactoside was identical to the above procedure except that one gram of DEAE-coated Kimal TM is substituted for the immobilized modified protein. No absorbance change is observed over a 15 minute period.

The activity for the support immobilized modified galactosidase-like protein is calculated according to the following formula:

$$\text{Activity} = \frac{(\text{change in } A/\text{minute})(10^6)(V_s)(2.6)}{(3200)(\text{weight of sample})}$$

wherein:
change in A/minute is change in absorbance per minute;
$10^6$ is micromoles/mole;
$V_s$ is the volume of the sample in liters;
2.6 is the density of the alumina in grams per liters; and
3200 is the extinction coefficient of o-nitrophenol in liters/mole.

The assay results are as follows:

| | Substrate |
|---|---|
| | Galactoside (U/ml support) |
| Initial Activity | 0.0 |
| Final Activity | 0.59 |

The results show that the galactosidase-like modified protein prepared according to the present invention exhibited enzymatic activity with respect to o-nitrophenyl-beta-D-galactoside substrate. No activity is previously detected in the native catalase. This illustrates the conversion of one genus of enzyme, a bovine catalase of the oxidoreductase family to a galactosidase enzyme-like modified protein.

EXAMPLE 6

Two hundred fifty mg of catalase, from Sigma type C-40, lot 109 C-7370 is dissolved in 200 ml of distilled, deionized water. Next, 250 mg of D-galactal inhibitor for galactosidasepurchased from Koch-Light Laboratories, Ltd. lot 56129, code 2836 h is added to the catalase. The solution is slowly stirred for one hour at 25° C. with the resulting pH of 6.5.

The inhibitor-native catalase solution is subjected to partial denaturation conditions as follows. Fifty mg of succinic anhydride is dissolved in one ml of acetone. Next, 0.3 ml of the succinic anhydride solution is added to the enzyme-inhibitor solution prepared above with slow stirring at 25° C. The solution is maintained at slow stir for one hour over which time the solution turns green in color. Next, 7.5 mg of diaminopropane HCl is added and the pH is determined to be 4.7. The solution is then allowed to stir one additional hour.

The partially denatured inhibitor bound enzyme produced above is immobilized as follows. The pH of the above solution is raised to 7 over a 15 minute period with the addition of about 3 ml of 0.1 M NaOH. Over the next one hour, the pH is raised to 8 with the dropwise addition of approximately 2 ml of 0.1 M NaOH. Next, 25 g of Kimal TM DEAE-dextran alumina support (−40+50 mesh) from Owens Ill., Inc., Toledo, Ohio (prepared as in Example 5) is washed with distilled, deionized water and the pH of the alumina supernatant liquid is raised to 8, with 0.01 M NaOH. The enzyme containing solution and the DEAE-dextran coated alumina support are then admixed and shaken slowly for about an hour. Next, 700 mg of 1-ethyl 3-(3dimethylaminopropyl) carbodiimide hydrochloride (EDC) is added and the result mixture is placed in a water bath at 0°-5° C. The solution is shaken slowly for about 1 hour with the temperature of the solution being lowered to 3° over the one hour. Next, one additional g of the EDC is added. The resulting mixture is allowed to react overnight (about 17 hours) and is subsequently washed with distilled, deionized water and assayed for enzymatic activity.

The sample prepared according to the process of the present invention is assayed for enzyme-like modified protein activity according to the procedure disclosed in Example 5 above. The sole change from the Example 5 procedue, formulas and particulars disclosed in the procedure for Example 5 is the substitution of 10 ml of 0.003 M sodium phosphate buffer at pH 7.5 for the 10 ml of 0.002 M sodium phosphate buffer at 7.5 used in Example 5. All other details of the assay for the present Example are identical to the procedures disclosed in Example 5 above.

|  | Substrate |  |
| --- | --- | --- |
|  |  | Galactoside (U/ml Support) |
| Initial Activity |  | 0.00 |
| Final Activity | Assay #1 | 0.66 |
|  | Assay #2 | 0.62 |

The results show that the galactosidase enzyme-like modified protein prepared according to the present invention exhibits activity toward the galactoside substrate for galactosidase enzymes. No activity was detected in the native catalase enzyme. This illustrates the conversion of one genus of enzymatic protein, namely a catalase, of the oxidoreductase family to a galactosidase enzyme-like modified protein.

EXAMPLE 7

To demonstrate that native ribonuclease enzyme shows no catalytic activity with respect to L tryptophan methyl ester (TME) substrate of Examples 2-4 above, the following control is performed.

Sixty mg of ribonuclease enzyme, from Sigma Chemical Company, Type R-5000, lot 20F 2010, is dissolved in 100 ml of 1 mM tris buffer, at pH 7, with slow stirring at 25° C.

The ribonuclease containing solution is then dialyzed using a No. 3 Spectra/Por ® dialysis tube against 3500 ml of 1 mM tris buffer, pH 7, for 17 hours at 0°-5°. The No. 3 tubing has a molecular weight exclusion range of 35-4500 daltons. Next, 1 ml of the ribonuclease containing solution is assayed versus TME substrate for possible enzymatic activity with respect to TME. The assay is conducted as follows.

A high pressure liquid chromatography system is used for the assay. The column is a 2 mm×25 cm stainless steel column packed with porous silica containing carboxyl side chains having an average pore size of 40 microns, purchased from Baker Chemical Company. The column eluant is 0.03 M acetate, pH 6, at a flow rate of 7 ml/min. The absorbance of the column outflow is monitored at 280 nm.

The assay sample solution containing native ribonuclease is prepared as follows. Eight ml of one mM tris buffer, pH 7.50, is admixed with one ml of 0.1 M TME, pH 3.2 and 1 ml of the ribonuclease solution prepared above. The assay control solution is prepared by admixing 8 ml of 1 mM tris buffer, pH 7.5; one ml of 0.1 M TME, pH 3.2 and one ml of one mM tris buffer, pH 7.0. The pH of the control and assay solutions is 5.8.

Next, one ml of the assay sample solution is removed from the sample beaker using a 2 ml hypodermic syringe with an 18 gauge needle and injected onto the column through a 20 microliter injection sample loop. The time of injection is recorded.

This procedure is then repeated using the assay control solution. Both sample and control solutions are chromatographed four times in order to obtain a plot of molarity of TME versus time for sample and control solutions.

A statistical analysis of the data obtained shows virtually identical slopes of $0.0620 \pm 0.005$ for both control and sample solutions. Accordingly, the native ribonuclease shows no measurable catalytic activity properties with respect to the TME substrate.

EXAMPLE 8

To demonstrate that native bovine serum albumin (BSA) shows no catalytic activity with respect to L-tryptophan methyl ester (TME) substrate of Example 1 above, the following control is performed.

One hundred mg of BSA from Sigma Chemical Company, No. 7511, lot 90F-8351, is dissolved in 100 ml of 1 mM tris buffer at pH 7, with slow stirring at 25° C.

The BSA containing solution is then dialyzed using a No. 2 Specrta/Por ® dialysis tube against 3500 ml of 1 mM tris buffer, pH 7, for 17 hours at 0°-5° C. The No. 2 tubing has a molecular weight exclusion range of 12-14,000 daltons. Next, one ml of the ribonuclease containing solution is assayed versus TME substrate for possible enzymatic activity with respect to TME. The assay is conducted as follows.

A high pressure liquid chromatography system is used for the assay. The column is a 2 mm×25 cm stainless steel column packed with porous silica containing carboxyl side chains having an average pore size of 40 microns, purchased from Baker Chemical Company. The column eluant is 0.03 M acetate, pH 6, at a flow rate of 7 ml/min. The absorbance of the column outflow is monitored at 280 nm.

The assay sample solution containing native BSA is prepared as follows. Eight ml of one mM tris buffer, pH 7.5 is admixed with one ml of 0.1 M TME, pH 3.2 and one ml of the ribonuclease solution prepared above. The assay control solution is prepared by admixing 8 ml of one mM tris buffer, pH 7.5; one ml of 0.1 M TME, pH 3.2 and one ml of one mM tris buffer, pH 7.0. The pH of the control and assay solutions is 5.8.

Next, one ml of the assay sample solution is removed from the sample beaker using a 2 ml hypodermic syringe with an 18 gauge needle and injected onto the column through a 20 microliter injection sample loop. The time of injection is recorded.

This procedure is then repeated using the assay control solution. Both sample and control solutions are chromatographed four times in order to obtain a plot of molarity of TME versus time for sample and control solutions.

A statistical analysis of the data obtained shows virtually identical slopes of $0.06 \pm 0.0065$ for both control and sample solutions. Accordingly, the native ribonuclease shows no measurable catalytic activity properties with respect to the TME substrate.

EXAMPLE 9

To demonstrate that native catalase shows no catalytic activity with respect to p-nitrophenyl-beta-D galactoside (NBG) substrate of Examples 5 and 6 above the following control is performed.

Two hundred fifty mg of catalase, purchased from Sigma Chemical Company, Type 7275, is dissolved in 25 ml of 0.5 mM acetate buffer, pH 4, with slow stirring at 25° C. The solution is placed in a No. 2 Spectra/- Por ® dialysis tube and dialyzed against 3500 ml of 5 mM acetate buffer, at pH 4 for 17 hours at 0.5° C. The No. 2 tubing has a molecular weight exclusion range of 12–14,000 daltons. Next, 0.2 ml of this assay sample is withdrawn and assayed versus NBG substrate for possible enzymatic activity of ribonuclease toward NBG. The assay is conducted as follows.

The assay sample mixture for assay is prepared by admixing 2.4 ml of 0.03 M sodium phosphate buffer containing 50 ppm antibacterial agent (Bioban brand antibacterial agent purchased from International Minerals and Chemicals Corp.) with 0.5 ml of 0.014 M NBG in a 3 ml cuvette. The cuvette is next placed in a ACTA III Spectrophotometer (from Beckman Instruments Company) wherein a straight base line is recorded for three min. The absorbance is monitored at 405 nm. Next, 0.1 ml of catalase solution is added to the NBG substrate solution in the cuvette. The cuvette is inverted four times to insure a homogeneous mixture in the cuvette and is placed back in the spectrophotometer for further measurement. The absorbance change is recorded over a 20 minute experimental period, no measurable catalytic activity properties with respect to NBG substrate are found in the native catalase.

I claim:

1. A process for chemically altering the substrate specifity of a native protein to produce an immobilized enzyme-like modified protein comprising:
   a. selecting an enzyme to be modeled;
   b. partially denaturing a native protein in the presence of an inhibitor for said model enzyme to form a partially denatured native protein model enzyme inhibitor complex;
   c. contacting said partially denatured protein-model enzyme inhibitor complex with a solid support for a time sufficient and at a temperature sufficient to absorb and immobilize said partially denatured protein-model enzyme inhibitor complex on said solid support and
   d. cross-linking said absorbed, immmobilized protein-model enzyme inhibitor complex to form an immobilized enzyme-like modified protein.

2. The invention defined in claim, 1 wherein said native protein is partially denatured by forming an aqueous solution of said native protein and maintaining said aqueous solution at a temperature and for a time sufficient to partially denature said native protein.

3. The invention defined in claim 1 wherein said native protein is partially denatured by admixing said native protein with water to form an aqueous solution and admixing the resulting solution with a denaturing agent.

4. The invention defined in claim 3 wherein said denaturing agent is an inorganic acid.

5. The invention defined in claim 3 wherein said denaturing agent is an organic acid.

6. The invention defined in claim 3 wherein said denaturing agent is an inorganic salt.

7. The invention defined in claim 3 wherein said denaturing agent is a water-miscible organic solvent.

8. The invention defined in claim 1 wherein said solid support in a porous, particulate alumina ceramic oxide.

9. The invention defined in claim 1 wherein said immobilized protein is cross-linked by admixing said immobilized protein with a cross-linking agent.

10. The invention defined in claim 9 wherein said cross-linking agent is glutaraldehyde.

11. The invention defined in claim 9 wherein said cross-linking agent is ethyl-3-(3-dimethylaminopropyl)-carbodiimide.

12. The invention defined in claim 9 wherein said cross-linking reagent is a mixture of and organic diamine and an organic carbodiimide.

13. The invention of claim 12 wherein said diamine is diaminopropane-HCl and said carbodiimide is ethyl-3-(3-dimethylaminopropyl)-carbodiimide.

14. The invention defined in claim 1 wherein said partially denatured protein-model enzyme inhibitor complex is admixed with an organic acid anhydride prior to admixture with said solid support.

15. A process for chemically altering the substrate specificity of a native protein to produce an immobilized enzyme-like modified protein comprising:
   a. selecting an enzyme to be modeled;
   b. adsorbing a native protein onto a solid support to immobilize the native protein;
   c. partially denaturing said adsorbed native protein and
   d. cross-linking said partially denatured adsorbed protein in the presence of an inhibitor for said model enzyme to form an immobilized enzyme-like modified protein.

16. The invention defined in claim 15 wherein said native protein is partially denatured by forming an aqueous solution of said native protein and maintaining said aqueous solution at a temperature and for a time sufficient to partially denature said native protein.

17. The invention defined in claim 15 wherein said native protein is partially denatured by admixing said native protein with water to form an aqueous solution and admixing the resulting solution with a denaturing agent.

18. The invention defined in claim 17 wherein said denaturing agent is an inorganic acid.

19. The invention defined in claim 17 wherein said denaturing agent is an organic acid.

20. The invention defined in claim 17 wherein said denaturing agent is an inorganic salt.

21. The invention defined in claim 17 wherein said denaturing agent is a water-miscible organic solvent.

22. The invention defined in claim 15 wherein said solid support in porous, particulate alumina ceramic oxide.

23. The invention defined in claim 15 wherein said immobilized protein is cross-linked by admixing said immobilized protein with a cross-linking agent.

24. The invention defined in claim 23 wherein said cross-linking agent is glutaraldehyde.

25. The invention defined in claim 23 wherein said cross-linking agent is ethyl-3-(3-dimethylaminopropyl)-carbodiimide.

26. The invention defined in claim 23 wherein said cross-linking agent is a mixture of an organic diamine and an organic carbodiimide.

27. The invention defined in claim 26 wherein said organic diamine is diaminopropane-HCl and said organic carbodiimide is ethyl-3-(3-dimethylaminopropyl)-carbodiimide.

28. The invention defined in claim 15 wherein said native protein is admixed with an organic anhydride prior to admixture with said solid support.

29. A process for chemically altering the substrate specificity of a native protein to produce an immobilized enzyme-like modified protein comprising:
   a. selecting an enzyme to be modeled;
   b. partially denaturing a native protein;
   c. contacting said partially denatured native protein with a solid support for a time sufficient and at a temperature sufficient to adsorb and immobilize said partially denatured protein on said solid support and
   d. cross-linking said partially denatured adsorbed protein in the presence of an inhibitor for said model enzyme to form an immobilized enzyme-like modified protein.

30. The invention defined in claim 29 wherein said native protein is partially denatured by forming an aqueous solution of said native protein and maintaining said aqueous solution at a temperature and for a time sufficient to partially denature said native protein.

31. The invention defined in claim 29 wherein said native protein is partially denatured by admixing said native protein with water to form an aqueous solution and admixing the resulting solution with a denaturing agent.

32. The invention defined in claim 31 wherein said denaturing agent is an inorganic acid.

33. The invention defined in claim 31 wherein said denaturing agent is an organic acid 34. The invention defined in claim 31 wherein said denaturing agent is an inorganic salt.

35. The invention defined in claim 31 wherein said denaturing agent is a water-miscible organic solvent.

36. The invention defined in claim 29 wherein said solid support in a porous, particulate alumina ceramic oxide.

37. The invention defined in claim 29 wherein said immobilized protein is cross-linked by admixing said immobilized protein with a cross-linking agent.

38. The invention defined in claim 37 wherein said cross-linking agent is glutaraldehyde.

39. The invention defined in claim 37 wherein said cross-linking agent is ethyl-3-(3-dimethylaminopropyl)-carbodiimide.

40. The invention defined in claim 37 wherein said cross-linking agent is a mixture of an organic diamine and an organic carbodiimide.

41. The invention defined in claim 40 wherein said organic diamine is diaminopropane HCl and said organic carbodiimide is ethyl-3-(3-dimethylaminopropyl)-carbodiimide.

42. The invention defined in claim 29 wherein said native protein is admixed with an organic anhydride after partial denaturation and prior to adsorption on said solid support.

43. A process for chemically altering the substrate specificity of a native protein to produce an immobilized enzyme-like modified protein, wherein said native protein has at least three disulphide groups per molecule, comprising:
   a. selecting an enzyme to be modeled;
   b. admixing said disulphide group containing native protein with a disulphide bridge reduction agent in the presence of an inhibitor for said enzyme to form a partially denatured native protein-model enzyme inhibitor complex;
   c. contacting said complex with a solid support for a time sufficient at a temperature sufficient to adsorb and immobilize said complex on said support and
   d. admixing said immobilized native protein-model enzyme inhibitor complex with a sulfhydryl oxidation agent for a time and at a temperature sufficient to form disulphide bonds in said protein to produce a modified enzyme-like protein.

44. The invention defined in claim 43 wherein said disulphide bridge reduction agent is beta-mercaptoethanol.

45. The invention defined in claim 43 wherein said disulphide bridge oxidation agent is an aqueous solution containing molecular oxygen wherein said solution is above pH 7.

46. The product of the process of claim 1.
47. The product of the process of claim 15.
48. The product of the process of claim 29.
49. The product of the process of claim 43.

* * * * *